United States Patent [19]

Narciso, Jr.

[11] Patent Number: 5,429,634
[45] Date of Patent: Jul. 4, 1995

[54] BIOGENIC IMPLANT FOR DRUG DELIVERY AND METHOD

[75] Inventor: Hugh L. Narciso, Jr., Santa Barbara, Calif.

[73] Assignee: PDT Systems, Santa Barbara, Calif.

[21] Appl. No.: 119,407

[22] Filed: Sep. 9, 1993

[51] Int. Cl.⁶ .............................................. A61K 9/00
[52] U.S. Cl. .................. 604/890.1; 424/422; 424/423
[58] Field of Search ............ 604/8, 9, 10, 890.1, 604/891.1, 892.1; 424/422, 423, 424, 425, 426, 427, 428

[56] References Cited

U.S. PATENT DOCUMENTS

| | | | |
|---|---|---|---|
| 4,849,226 | 7/1989 | Gale | 604/890.1 X |
| 4,895,724 | 1/1990 | Cardinal et al. | 604/891.1 X |
| 5,024,841 | 6/1991 | Chu et al. | 604/890.1 X |
| 5,110,604 | 5/1992 | Chu et al. | 604/890.1 X |
| 5,169,395 | 12/1992 | Narciso, Jr. | |
| 5,264,214 | 11/1993 | Rhee et al. | 604/891.1 X |
| 5,282,823 | 2/1994 | Schwartz et al. | 604/890.1 X |

Primary Examiner—Sam Rimell
Attorney, Agent, or Firm—Michael G. Petit

[57] ABSTRACT

A medicament-dispensing medical implant is described which is fabricated from relatively non-inflammatory biogenic tissue or biopolymers for implantation in or adjacent to a target issue in the human body. The implant, whic is non-thrombogenic, optically transluscent and relatively non-inflammatory, delivers relatively high doses of one or a combination of medicaments locally in a sustained fashion while systemically delivering a relatively low dose of said medicament(s). In one embodiment, a biogenic tissue such as endothelium from the interior of an artery of a donor animal is first stabilized by appropriate chemical treatment, then burdened with a medicament. The implant, which is preferably in the form of a stent, plug or a patch, releases the medicament over a period of time. Desirable sequellae to the implantation of the device includes the relative absence of an inflammatory response when compared to synthetic implants and reendotheliazation of the implant with autologous endothelium which encapsulates and anatomically stabilizes the implant.

3 Claims, 4 Drawing Sheets

BIOGENIC IMPLANT FOR DRUG DELIVERY AND METHOD

BACKGROUND OF THE INVENTION

1. Field of the Invention

This invention relates generally to an implantable device for the sustained delivery of a medicament and, more particularly, to a device and method for preventing restenosis following atherectomy.

2. Reference to a Related Patent Application

Reference is made to a copending patent application Ser. No. 08/002,209 filed Jan. 8, 1983, entitled: "Medicament Dispensing Stent for Prevention of Restenosis of a Blood Vessel" by the present inventor.

3. Prior Art

Cardiovascular disease (CVD) is the leading cause of death in the U.S. One commonly used method of treating CVD is angioplasty/atherectomy (mechanical or laser). While angioplasty/atherectomy is acutely successful in relieving the symptoms of CVD, the procedure is limited by a high rate of arterial reclosure or restenosis. Various methods of preventing restenosis have been tested with little success reported to date.

One possible treatment for the prevention of restenosis is Photodynamic Therapy (PDT), also known as Photoatherolytic (PAL) Therapy when referring to vascular applications of PDT. PAL Therapy requires the delivery of a photosensitizing drug to the stenosing atheroma which is selectively retained by the proliferating component of atheromatous plaques which is believed to be the cell type responsible for restenosis. Once sequestered in the problematic proliferating cells, the drug is converted from its ground or dormant state to an excited, highly toxic state by the absorption of light energy at a very specific wavelength. A currently preferred therapeutic modality consists of administering the photosensitizer (PS) drug systemically in a single-dose bolus. Since the drug is initially delivered to all cells of the body, a delay time is required to allow the PS drug to clear from normal cells while it is retained by the proliferating cells prior to activation with light.

Since restenosis is a complex process which can begin immediately after therapeutic intervention (angioplasty/atherectomy) and continue for months post intervention, it is desirable to provide a device and method capable of providing the sustained delivery of a PS drug to inhibit the proliferation of smooth muscle cells and ultimately to lyse the PS ladened cells with therapeutic light energy.

One approach to the problem of sustained long term drug delivery employs implantable biodegradable polymer/drug combinations in a variety of ways to achieve a controlled regular or continuous administration of the drug. Biodegradable polymers are useful as carriers for many different types of drugs because they serve as a temporary matrix to hold the drug, but do not chemically interact with the drug. As the matrix erodes, the drugs are released and can diffuse into the tissues.

In one prior art embodiment, a synthetic (non-biogenic) biodegradable polymer matrix is homogeneously impregnated with a medicament so that the medicament is released more or less continuously and uniformly as the supporting polymer matrix erodes. In another variation of this basic idea, a single reservoir of the drug or medicament in solution is encapsulated by a semi-porous polymer matrix. The drug diffuses continuously out of the reservoir, through the polymer, and finally to the intended delivery area. Metal stents coated with bioabsorbable synthetic polymer have also been used to deliver medicament but such metal stents are optically opaque and thrombogenic. In still a further variation, tiny discrete "pockets" of the drug are encapsulated throughout the synthetic polymer. If the polymer is biodegradable then it will completely dissolve thereby releasing all of the impregnated or encapsulated drug. The above prior art devices are known in the art and are made from synthetic polymers. The problems with implants fabricated using non-biogenic material are that such prior art implants are thrombogenic and being a "foreign body" stimulate the host's inflammatory response.

Such devices can also be constructed from naturally occurring biopolymers and derivatives thereof or biogenic tissue. Biological materials such as bovine and porcine tissues harvested from donor animals are commonly used for implantation into the human body. They are known to be non-thrombogenic and non-inflammatory. The porcine heart valve is one such example. Such biogenic tissues are well received and well tolerated by the host human tissues and, unlike biodegradable synthetic polymers, biogenic tissue implants are less likely to induce an inflammatory host response and are replaced over time by the host natural tissue produced in situ. Human tissues harvested from a human donor (autologous or heterologous) are also viable tissue types for this device.

Cancer is the second leading cause of death in the U.S. A stent-type device for the slow sustained delivery of an appropriate medicament to cancers on a luminal wall such as esophageal cancer, and a patch or plug-type of device for implantation within bulk tumors is desired. Preferably, such a stent, plug or patch should be minimally inflammatory, non-thrombogenic, optically transluscent, biologically compatible and capable of sustained drug delivery to a localized area of a tubular tissue over the period of time required to effect a permanent therapy.

SUMMARY

PAL Therapy is believed to be potentially effective for the prevention of restenosis. PDT has also been demonstrated to be very effective in the treatment of various cancers. In one embodiment, a stent-type device made from biogenic tissue and/or biopolymers is described which can be used to deliver a PS drug locally to a target tissue over a period of time. In another embodiment, a plug-type of implantable device is described which can be embedded in solid tissue thereafter to deliver medicament to a target. In still another embodiment the implant may take the form of a substantially planar patch.

In a particular preferred embodiment a medical implant is described for the local delivery of medicament to an intraluminal target tissue. The device and method involves the use of a bio-absorbable biogenic patch or stent which is impregnated or otherwise burdened with a photosensitizer drug, with or without complimentary medicaments, to locally deliver said drug(s) into target tissue on the vessel wall over a prolonged period of time as the stent is absorbed. Although the use of bioabsorbable, non-biological, but biocompatible stents have been proposed for such a therapy and remain a viable solution, these materials are often inflammatory to the host tissue.

Accordingly, it is an object of this invention to produce a medicament dispensing implant which is non-thrombogenic, minimally inflammatory and generally well received and well tolerated by the human body.

It is another object of this invention to produce a medicament-dispensing implant which is absorbed by the body over time.

It is yet another object of this invention to produce a medicament-dispensing implant which can deliver medicaments substantially only to selected target tissues.

It is still another object of this invention to provide a biodegradable biogenic tissue implant which can deliver medicaments over a sustained period of time and be replaced by host tissue.

It is another object of this invention to describe a method in which this device can be used to locally deliver medicament(s) over a prolonged period of time.

It is still another object of this invention to describe a method in which this device can be used to locally deliver medicament(s) including a photosensitizer over a sustained period of time which is ultimately used in PDT.

The above referenced objectives are met by the present invention which is best understood by referring now to the preferred embodiments of the invention.

DESCRIPTION OF THE PREFERRED EMBODIMENTS

Preparation of the Biogenic Tissue

Biogenic tissue such as endothelium from the innermost layer of an artery (intima), collagen, fibrin, etc. is surgically removed from a donor animal such as swine or a human donor (autologous or heterologous) and maintained in a nutrient rich solution. These viable tissues can then be "fixed" using a stabilized glutaraldehyde process at pressures less than 2 mm Hg that is well known in the art and used for such implants as replacement porcine heart valves.

Alternatively, biogenic macromolecules (alternatively referred herein as "biopolymers"), such as a collagen, chitin, chitosan or cellulose may also be used to fabricate a biogenic implant. Chitin, for example, comprises the bulk of the organic material in arthropod exoskeletons such as crab shell. If the exoskeleton is demineralized using strong acid the remaining chitinous fraction may be extracted, deacetylated (if desired), and pressed in to the desired shape for implantation. Cellulose is a polymer comprising glucose rings derived from plants. Derivatives of cellulose which may be suitable for implantation include methylcellulose, ethylcellulose, hydroxyethylcellulose, hydroxypropylcellulose and sodium carboxymethylcellulose.

Preparation Of the Biogenic Implant

After the biogenic tissue has been prepared as described above, the biogenic tissue is soaked in a solution containing a relatively high concentration of the desired medicament(s) such as, for example, a photosensitizer (i.e. 0.1–1.0 mg of PS/ml solution—the desired concentration of PS in the device implantable will depend on the thickness of the lesion being treated and its location) for a period of 1–5 hours (the time will again depend on the tissue absorption characteristics and the location and application of the implant). The biogenic tissue is maintained at 37° C. during the PS drug-burdening process while excluding light at wavelengths which might activate the PS. Other medicaments may be added to the bath permeate the implant. One such drug which is potentially complimentary to the PS is heparin which has the characteristics being an anti-coagulant, anti-platelet, anti-fibrin, anti-collagen agent and may facilitate the prevention of restenosis. New molecules having Heparin—like activity may also be employed.

Method of Using the Biogenic Implant

Figure 1:
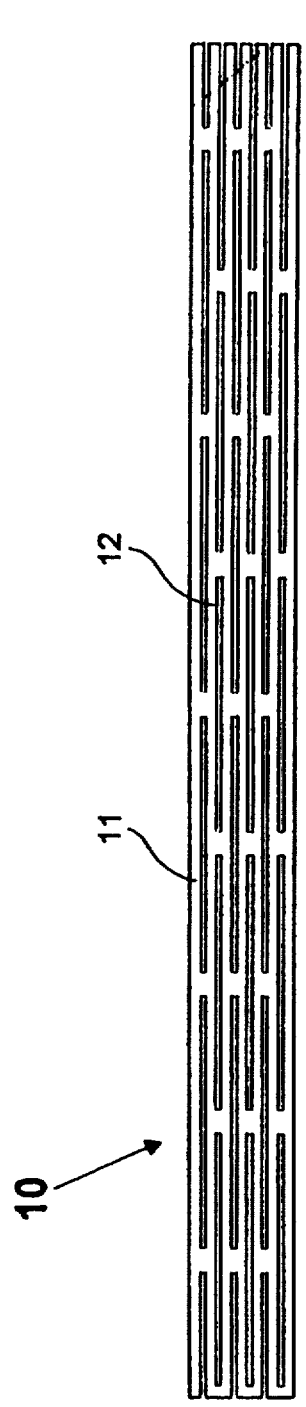
FIG. 1 is a side view of a medicament-dispensing implant in accordance with the present invention in the form of a stent.

An exemplary method for using the biogenic implant according to the present invention may taught by looking first at a stent as shown in FIG. 1. The stent 10 is a tubular member comprising a biogenic tissue 11 with medicament 12 incorporated therein. The medicament may be a photosensitizer which has been shown to be useful for preventing restenosis following atherectomy, or it may be any other medicament which is desirable to have released over a long period of time. The medicament may be encapsulated in discrete cells or evenly distributed throughout the body of the stent.

Figure 2:
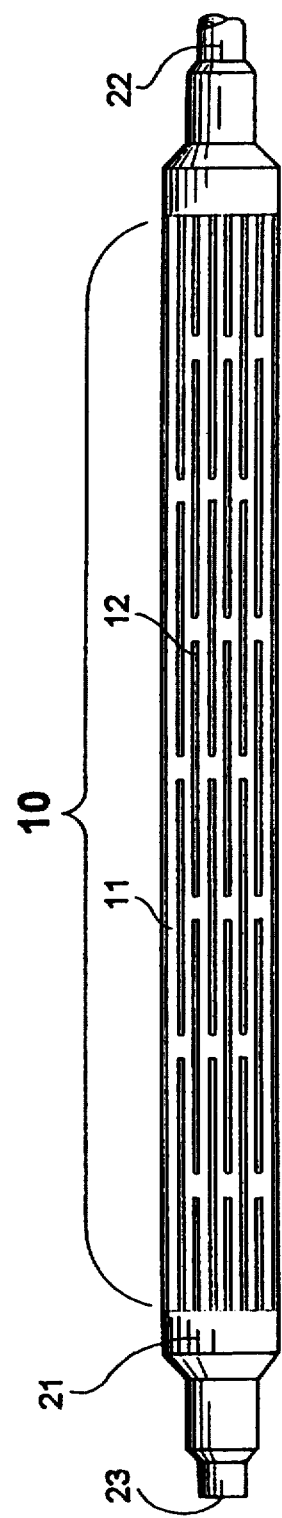
FIG. 2 shows the stent of FIG. 1 deployed on a balloon catheter.

Turning now to FIG. 2 we see the stent 10 with a balloon catheter 22 having a distal tip 23 inserted therein. The balloon catheter 22 has a balloon portion 21 which can be partially inflated so that the outer surface of the balloon portion 21 firmly and snugly engages the inner surface of the stent 10. A sheath (not shown) may or may not be used over the balloon/stent catheter to prevent the undesired deployment of the stent while advancing and positioning the catheter. Standard angioplasty procedures are used to deliver the stent through the femoral artery or other arterial point of entry and advancing the stent to the site of the target tissue.

Figure 3:
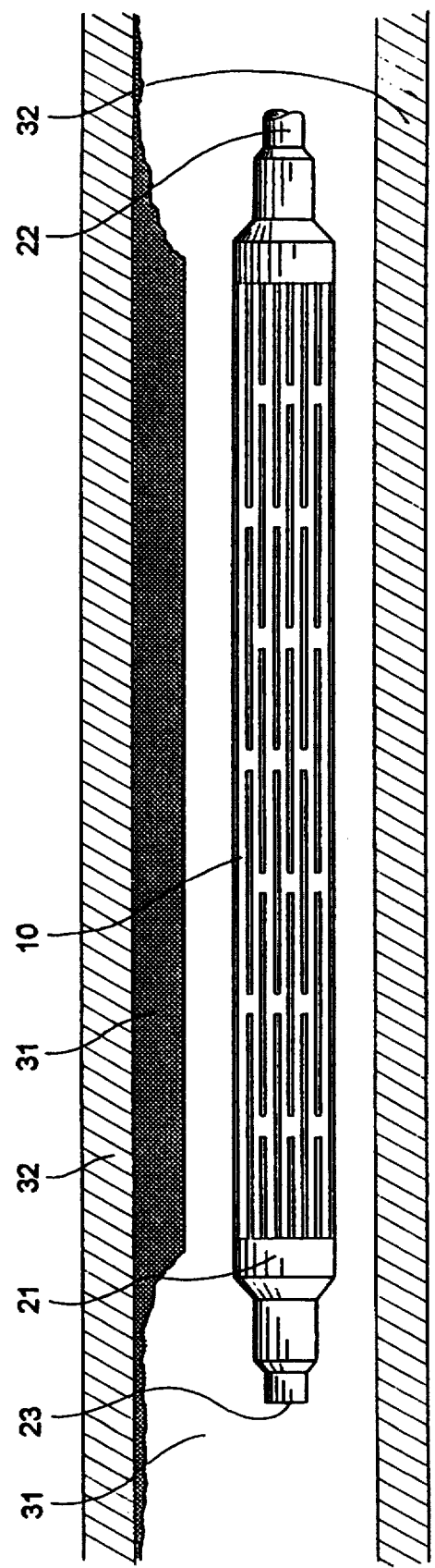
FIG. 3 is a cut-away view of a tubular tissue such as an artery housing the catheter of FIG. 2 with the balloon only partially inflated.
Figure 4:
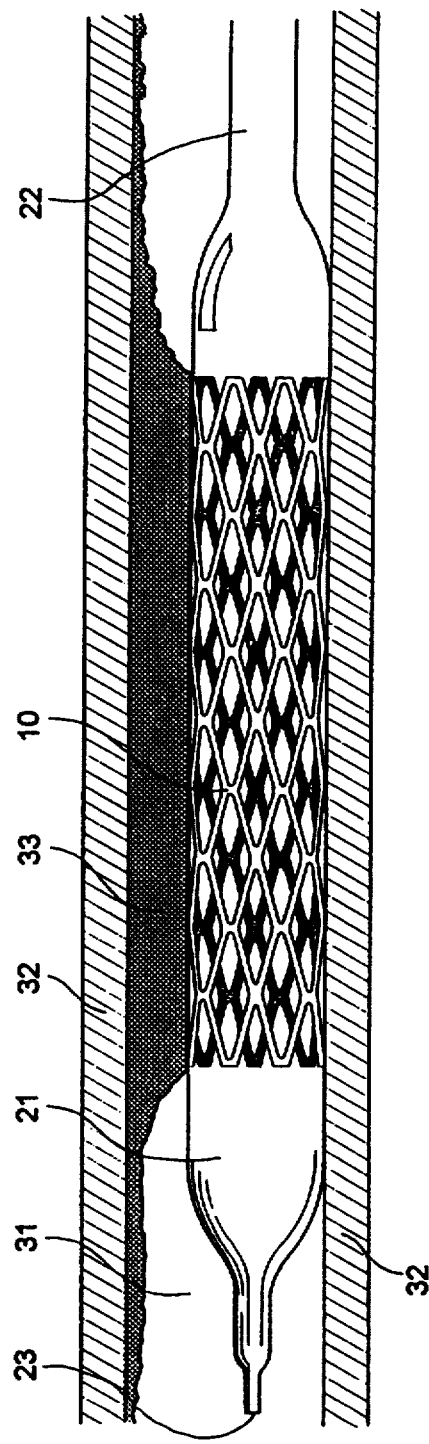
FIG. 4 is a cut-away view of a tubular tissue such as an artery housing the catheter of FIG. 2 with the balloon fully inflated.
Figure 5:
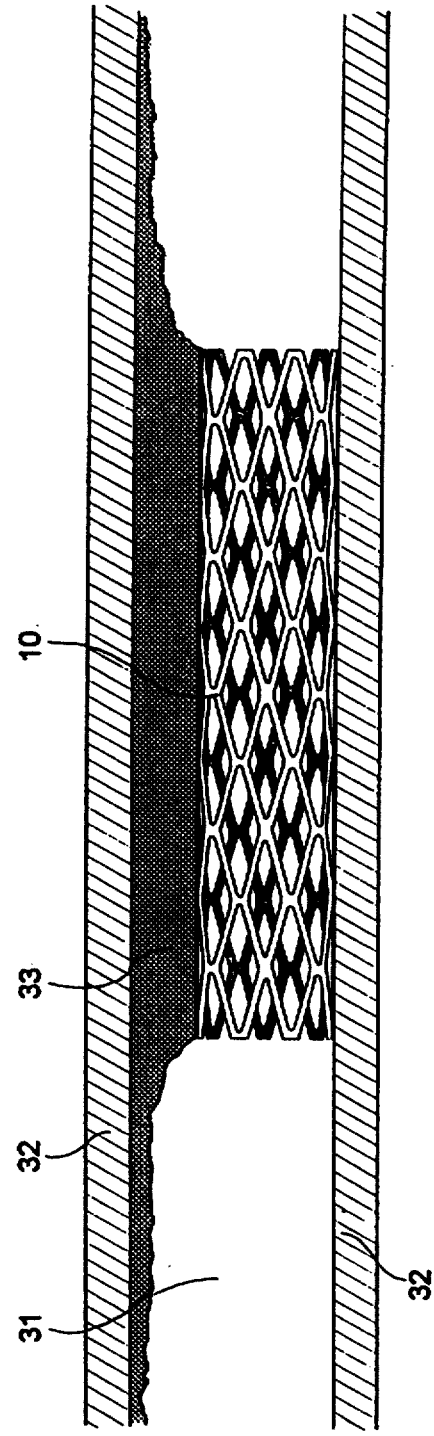
FIG. 5 shows a partially cut-away view of the artery with the stent deployed in the artery adjacent to the target tissue and with the catheter removed.
Figure 6:
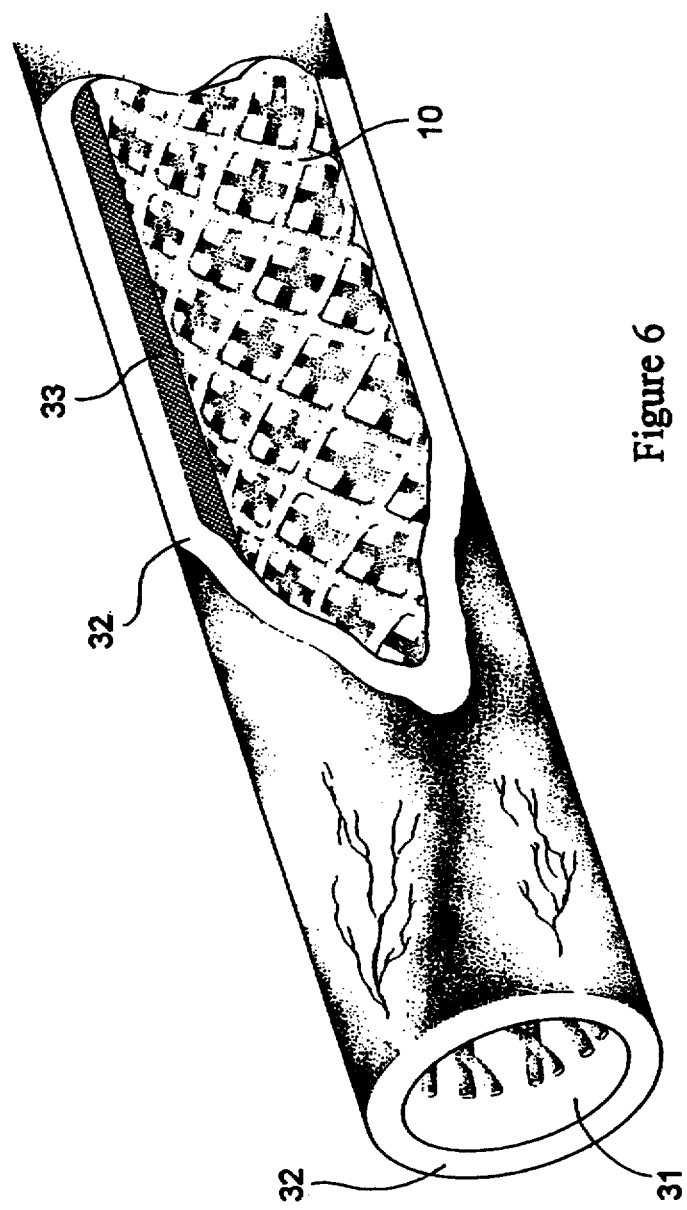
FIG. 6 is a partially cutaway perspective view of the artery showing the stent deployed within the artery as in FIG. 5.

In FIG. 3, a longitudinal, cross-sectional view of an arterial member is shown having an arterial wall 32 and a lumen 31. A atheromatous patch 31 on the wall 32 of the vessel (the "target tissue" in this example) has been partially removed to permit passage of the catheter 22 therethrough. The catheter 22 is advanced through the vessel until the balloon portion 21 directly underlies the area of the vessel in which it is desirable to deploy the stent 10. Once in position, the stent can be deployed by inflating the balloon member 21 so that the outer surface of the stent 10 pressed against the atheromatous lesion 31 on the wall of the vessel 32 as shown in FIG. 4. The expanded stent may then be "welded" to the atheromatous tissue 31 on the wall 32 of the vessel. This "welding" may be accomplished by the application of heat to the stent. Once the stent 10 has been deployed and adhered to the target tissue 31 and the wall of the vessel, the balloon portion 21 of the catheter 22 is deflated and catheter removed as shown in FIG. 5. In FIG. 6 we see a fragmentary section of the vessel wall with the stent deployed therein and the balloon catheter removed. With the foregoing description in mind, I present an example of the device and method used to prevent restenosis following atherectomy.

Example of Using the Biogenic Stent for Preventing Restenoisis

Following Atherectomy or Angioplasty

A drug-burdened biogenic implant in the tubular form of a stent 10 is loaded over a light diffusing catheter such as described by Narciso, Jr. in U.S. Pat. No. 5,169,395. A sheath may or may not be used over the balloon/stent catheter to prevent the undesired deployment of the stent while advancing and positioning the catheter.

To deploy the stent, standard angioplasty procedures are used to deliver the stent through the femoral artery or other arterial point of entry. In summary, following identification of the target tissue comprising atheromatous plaque on the wall of the vessel, the stent should be deployed in the area of injury and utilized according to the following steps:

a. the stent-deploying balloon catheter is positioned at the lesion site immediately after the completion of the angioplasty/atherectomy (the protective sheath should be pulled back to expose the PS-laden stent at this point if a sheath was used);

b. the balloon is expanded until the surface of the PS-ladened biogenic stent implant fully engages the arterial wall for the full 360°;

c. the tissue is irradiated through the transparent balloon wall with a wavelength of light (i.e. 800–1000 nm) which produces low level heating to cause the denaturation and "welding" of the biogenic stent to the host vessel. The wavelength of the light used should not be one which activates the PS in the stent. If the activation wavelength and the welding wavelength overlap, an alternative method of heating should be employed. As example of an alternative heating method, a radio frequency (RF) heated balloon or a balloon which incorporates circulating hot fluid may be employed to effect "welding". Alternatively, a photochemical cross-linking dye may be employed to facilitate the welding process. Such dyes include, for example, brominated 1, 8-naphthalimide compounds. These dyes are activated by visible light and, following activation, covalently bind to amino acid residues, both free and in proteins, rendering them useful as protein and peptide cross-linking agents. Care should be taken to choose a photochemical cross-linking dye with an activation wavelength which will not activate the PS if one is present. The absorption maximum for the naphthalimide compounds is around 420 nm, well removed from the activation wavelength of PS compounds used in PDT.

d. the balloon is then deflated and all catheters are removed from the body; and e. (Only used for PDT applications.) A predetermined time later, the PS which has been absorbed by the vessel should be activated by means of a suitable light delivery catheter such as the catheter described by Narciso, Jr. in U.S. Pat. No. 5,169,395 and using standard PAL Therapy techniques. The PS acts to inhibit the proliferation of cells post angioplasty thereby reducing restenosis.

The foregoing procedure for preventing restenosis is exemplary and not limiting Similar methods can be employed to deploy a stent in non-arterial lumens such as the colon or esophagus for PDT treatment of cancer. Once deployed in the artery or other tubular tissue of the host, the stent will locally deliver the medicament(s) to the lesion area over a sustained period of time (i.e. 2 weeks to 6 months). Two weeks post stent placement, re-endothelialization should occur covering the stent with natural autologous endothelium thus encapsulating the stent in the luminal wall.

If necessary, two weeks to six months following the deployment of the stent, the patient may be brought back to the catheterization laboratory. Using standard angioplasty techniques and an invasive intravascular light diffusing catheter, the lesion site can be irradiated to receive a dose of light sufficient to activate the PS causing cell lysis and cell necrosis.

Figure 7:
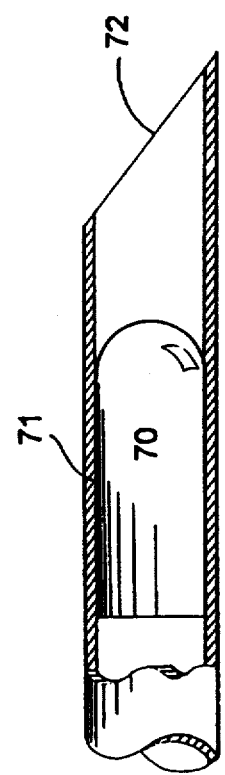
FIG. 7 is a partially cutaway perspective view of the shaft of a needle showing an implantable plug which is dimensioned to fit within the lumen of the hollow-bore needle for deployment.

The medicament-dispensing biogenic implant of the present invention may be formed into a patch or plug for insertion into a target tissue such as a solid tumor. Such a plug 70 is shown in FIG. 7. The plug 70 is dimensioned to fit within the bore of a needle 71 having a tip 72. The needle 71 may be inserted into the target tissue until the tip is embedded within or adjacent to the target tissue. The plug 70 may then be extruded through the tip 72 and the needle 71 removed.

While particular embodiments of the present invention have been illustrated and described, it would be obvious to those skilled in the art that various other changes and modifications can be made without departing from the scope of the invention. It is, therefore, intended to cover in the appended claims all such changes and modifications that are within the scope of the invention.

What I claim is:

1. A medicament dispensing medical implant for implantation within the body of a mammal comprising a biocompatible, bioabsorbable, biogenic material impregnated with at least one medicament and wherein said medicament is capable of being substantially released from said biocompatible, bioabsorbable, biogenic material and wherein said medicament is a photosensitizer drug.

2. The medical implant of claim 1 wherein said biogenic material is formed into a tubular stent.

3. The medical implant of claim 1 wherein said biogenic material is formed into a plug.

* * * * *